United States Patent
Wenstrom, Jr.

(10) Patent No.: US 6,767,037 B2
(45) Date of Patent: Jul. 27, 2004

(54) SLIDING AND LOCKING SURGICAL KNOT

(75) Inventor: Richard F. Wenstrom, Jr., Norwood, MA (US)

(73) Assignee: DePuy Mitek, Inc., Norwood, MA (US)

(*) Notice: Subject to any disclaimer, the term of this patent is extended or adjusted under 35 U.S.C. 154(b) by 0 days.

(21) Appl. No.: 09/966,565

(22) Filed: Sep. 27, 2001

(65) Prior Publication Data

US 2003/0060835 A1 Mar. 27, 2003

(51) Int. Cl.[7] .................. D04G 5/00; A61B 17/10; A61B 17/04
(52) U.S. Cl. .................. 289/1.2; 606/139; 606/144
(58) Field of Search ............ 606/72, 222, 224, 606/232, 148, 139, 144; 112/156, 416, 22; 289/1.2, 1.5, 3, 4

(56) References Cited

U.S. PATENT DOCUMENTS

| | | | |
|---|---|---|---|
| 4,779,616 A | * 10/1988 | Johnson | ...................... 606/148 |
| 5,178,629 A | 1/1993 | Kammerer | |
| 5,217,486 A | 6/1993 | Rice et al. | |
| 5,395,382 A | * 3/1995 | DiGiovanni et al. | ........ 606/148 |
| 5,405,352 A | 4/1995 | Weston | |
| 5,441,502 A | 8/1995 | Bartlett | |
| 5,472,446 A | 12/1995 | de la Torre | |
| 5,522,845 A | 6/1996 | Wenstrom, Jr. | |
| 5,527,323 A | * 6/1996 | Jervis et al. | ................. 606/148 |
| 5,549,618 A | 8/1996 | Fleenor et al. | |
| 5,609,597 A | * 3/1997 | Lehrer | ........................ 606/139 |
| 5,681,331 A | * 10/1997 | de la Torre et al. | ........ 606/148 |
| 5,749,879 A | * 5/1998 | Middleman et al. | ........ 606/139 |
| 5,752,964 A | * 5/1998 | Mericle | ...................... 606/148 |
| 5,782,866 A | 7/1998 | Wenstrom, Jr. | |
| 5,824,011 A | * 10/1998 | Stone et al. | ................. 606/232 |
| 5,893,592 A | * 4/1999 | Schulze et al. | ............... 289/1.2 |
| 6,143,006 A | 11/2000 | Chan | |

OTHER PUBLICATIONS

Clifford Ashley, The Ashley Book of Knots, 1944, Double-Day, The entire book is relevant. However, the most relevant sections were photocopied and placed in the file.*

* cited by examiner

Primary Examiner—Julian W. Woo
Assistant Examiner—Paul A Roberts
(74) Attorney, Agent, or Firm—Nutter McClennen & Fish LLP

(57) ABSTRACT

The present invention provides a sliding and locking knot that does not require an additional half hitch to lock and suture retaining structures having such a knot. The sliding and locking knot has a low knot profile suitable for use in surgical areas with low clearance and to avoid interference with surrounding tissue. Additionally, the sliding and locking knot maintains suture strength and is easy to form. Also provided are methods for anchoring tissue to a bony structure using the bone anchor and sliding and locking knot of the present invention.

17 Claims, 9 Drawing Sheets

SLIDING AND LOCKING SURGICAL KNOT

CROSS-REFERENCE TO RELATED APPLICATIONS

Not applicable.

STATEMENT REGARDING FEDERALLY SPONSORED RESEARCH

Not applicable.

FIELD OF THE INVENTION

The present invention relates generally to surgical knots and techniques for tying these knots and using the knots to fix tissue within a patient. More particularly, this invention relates to a sliding and locking surgical knot and a method for forming such a knot.

BACKGROUND OF THE INVENTION

The development of arthroscopic reconstructive procedures has required the passage of sutures and tying of knots down a cannula. Successful accomplishment of this goal requires both mastery of suture handling and knot tying techniques. Most sliding knots currently being used such as the Duncan loop, Roeder knot, and Tennessee slider are suitable for arthroscopic procedures, but all require the surgeon to throw additional half hitches to lock the knot or to prevent the knot from loosening. It is often difficult for the surgeon to maintain adequate tension on the sliding knot while throwing these extra hitches.

There is thus a need for a sliding and locking knot that can be used in arthroscopic surgeries that does not require an additional half hitch to lock. Also desirable is a sliding knot that does not affect suture strength, has a low knot profile, and a short learning curve to tie.

SUMMARY OF THE INVENTION

The present invention avoids the aforementioned problems associated with current knots by providing a sliding and locking knot that does not require an additional half hitch to lock and suture retaining structures having such a knot. The sliding and locking knot has a low knot profile suitable for use in surgical areas with low clearance and to avoid interference with surrounding tissue. The sliding and locking knot also maintains suture strength and is easy to form.

In one embodiment, the sliding and locking surgical knot comprises a filament and includes a post at a proximal-most end. Formed on the post is a major loop that extends to a free end at a distal-most portion of the filament. Free end is threaded through the major loop to form a minor loop. A portion of the free end encircles the major loop to form at least one coil that bisects the major loop in half. Free end is then threaded through the minor loop. The sliding and locking knot can be slid down by pulling on the post. The sliding knot can be locked without requiring an additional half hitch by pulling on the free end to close the coil around the major and minor loops and post.

The sliding and locking knot can also be connected to a suture anchor device for reattaching tissue to its surroundings. In an exemplary embodiment, the suture anchor device is a bone anchor having a body extending between a first leading end and a second trailing end, the body having thereon at least one bone engaging element. Within the body is a suture receiving aperture for receiving the sliding and locking surgical knot of the present invention.

Also provided are methods for anchoring tissue to a bony structure using the bone anchor and sliding and locking knot of the present invention. In one embodiment, the bone anchor includes a suture filament extending from the suture receiving aperture. The anchor can be inserted into a bone cavity within the bony structure with the suture filament extending out from the cavity. The torn or loose tissue can be brought proximate to the bone structure and the ends of the filament tied to form the sliding and locking knot of the present invention.

In another embodiment, the bone anchor includes a preformed sliding and locking knot within the suture receiving aperture. The bone anchor can be inserted into the bone cavity, while a free end of the tissue is placed through the major loop of the sliding and locking knot. When the tissue is proximate to the bone structure, the knot can be locked to effect attachment of the tissue to the bony surface.

Further features of the invention, its nature and various advantages, will be more apparent from the accompanying drawings and the following detailed description of the drawings and the preferred embodiments.

DETAILED DESCRIPTION OF THE DRAWINGS

Figure 1:
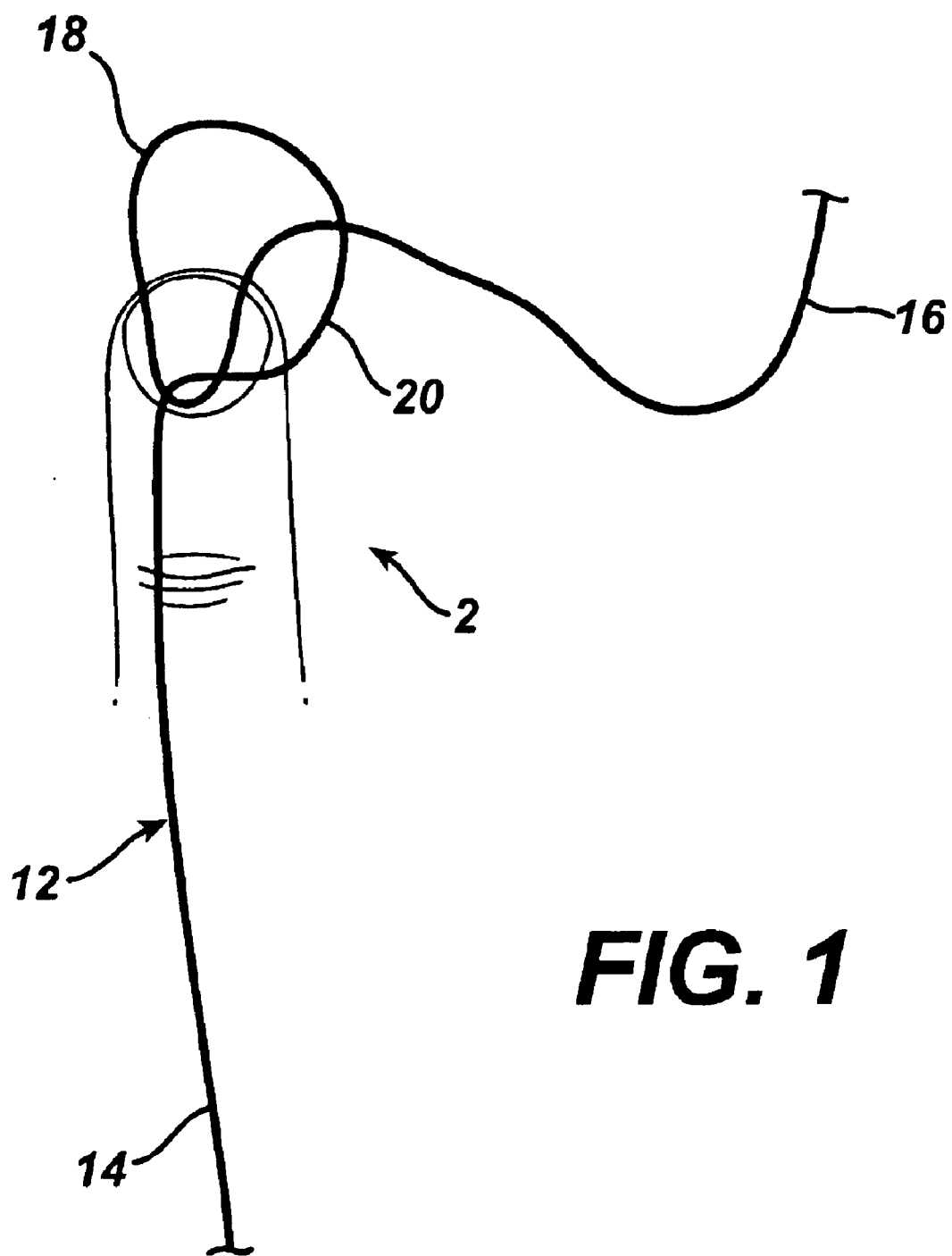
FIG. 1 shows a first step for forming the sliding and locking knot of the present invention.

The following description of a method of forming sliding and locking knot 10 of the present invention is made as if from the user's perspective looking straight forward at the suture strand or filament 12 in the user's hand. Referring to FIG. 1, the initial step for forming knot 10 involves the user holding a proximal-most portion 14 of the filament 12 in his hand, between the thumb 2 and index finger (not shown). The held portion may be considered the post 14 of the knot 10. With the opposite hand, the user then passes a distal-most end, or terminal end 16 of filament 12 behind the post 14 to form a first, or major loop 18. Illustrated thumb 2 may serve as a scale indicator for determining the size of major loop 18. As shown, first loop may be positioned approximately half-way along filament 12. However, it is contemplated that first loop 18 may be located anywhere along the length of the filament 12. Terminal end 16 is threaded through first loop 18 to resemble what is shown in loose formation in FIG. 1, creating a second, or minor loop 20.

Figure 2:
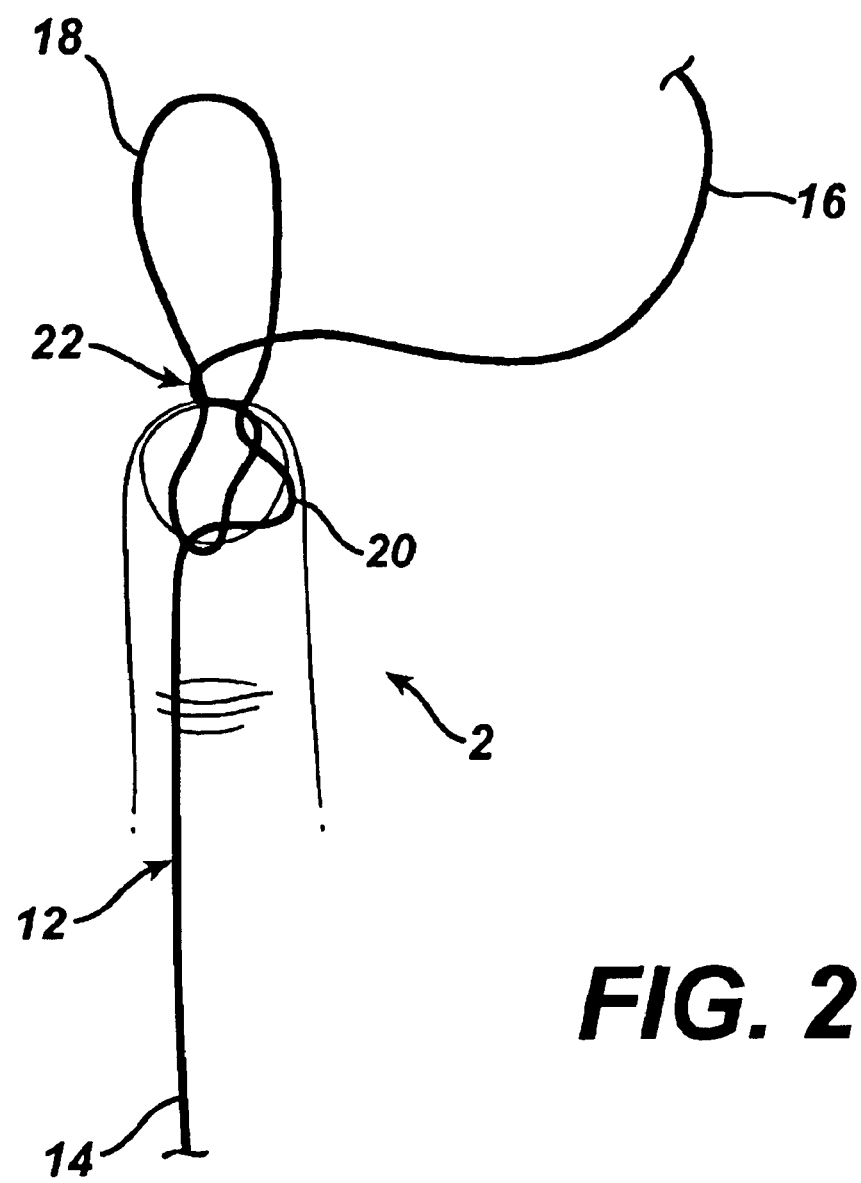
FIG. 2 shows the next step for forming the sliding and locking knot of the present invention.
Figure 3:
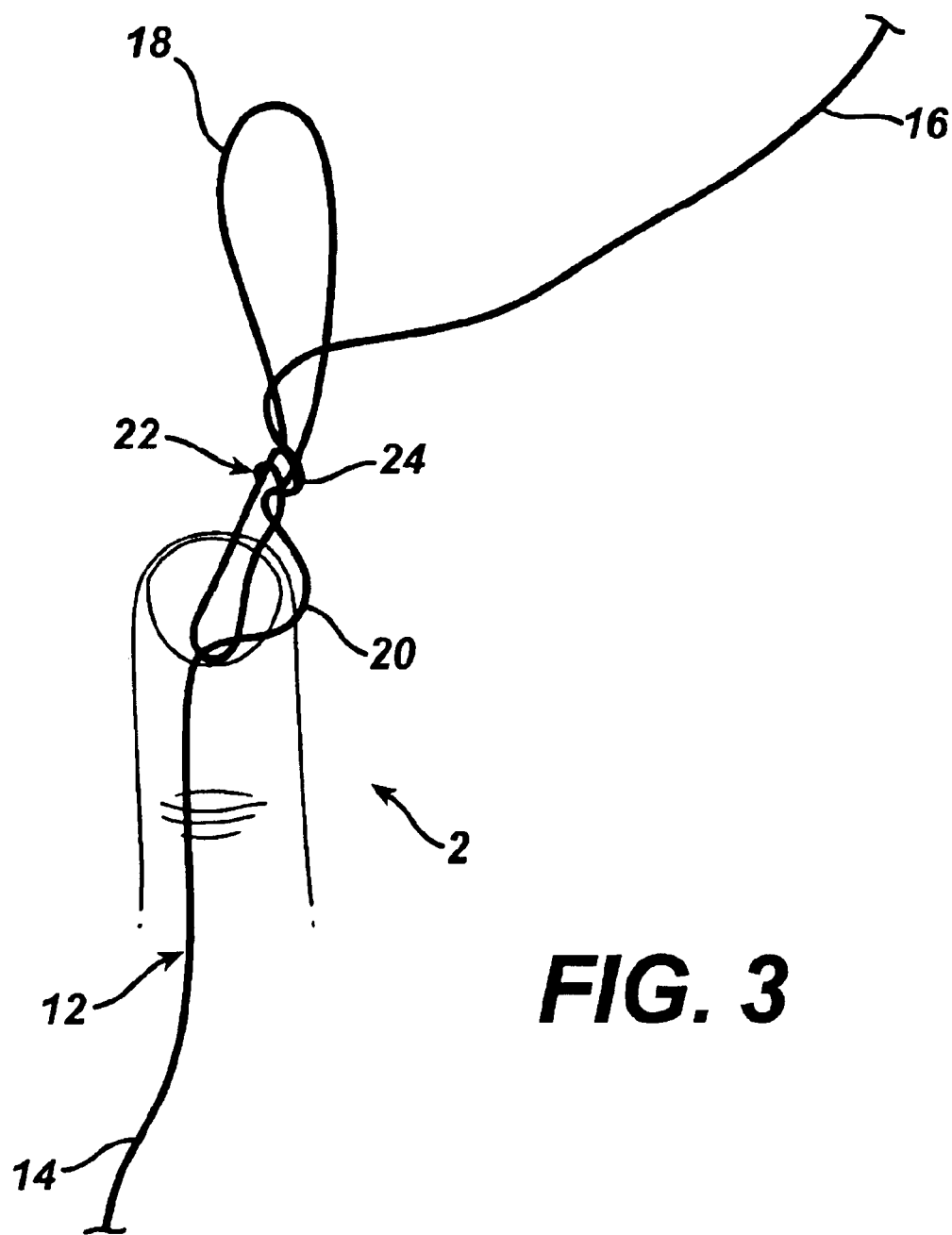
FIG. 3 shows another step for forming the sliding and locking knot of the present invention.
Figure 4:
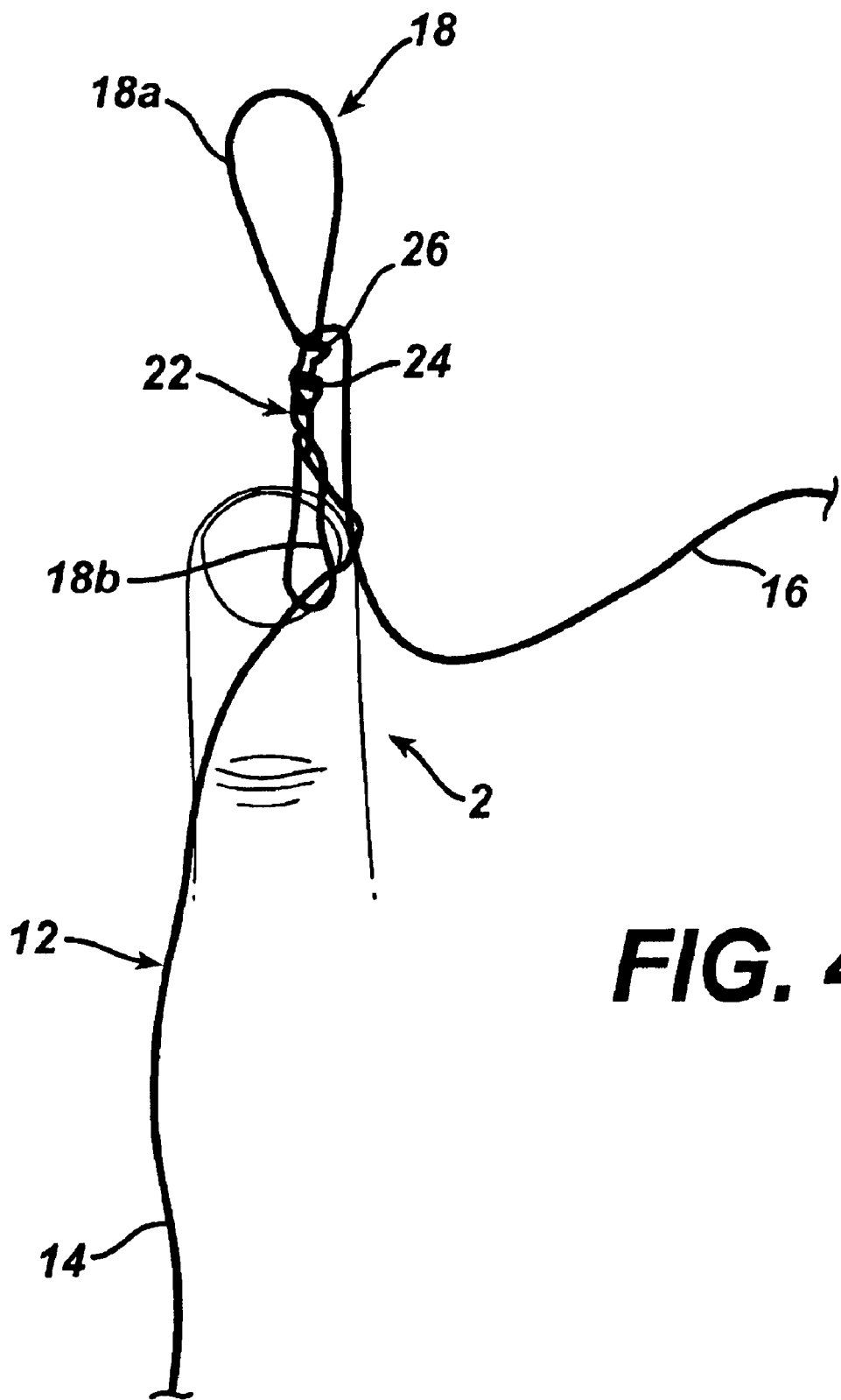
FIG. 4 shows yet another step for forming the sliding and locking knot of the present invention.

Terminal end 16 then wraps over and behind the first loop 18 to form a first coil 22 as shown in FIG. 2. In FIG. 3, the terminal end 16 is again wrapped over and behind the first loop 18, just above the first coil 22, to form a second coil 24. It is contemplated that about two to five coils may be created using this procedure, depending on the present needs of the surgeon. Referring to FIG. 4, three coils 22, 24, and 26, each spaced about one filament width apart from one another, are shown on first loop 18. Coils 22, 24, and 26 bisects first loop 18 into a distal loop 18*a* and a proximal loop 18*b*.

Figure 5:
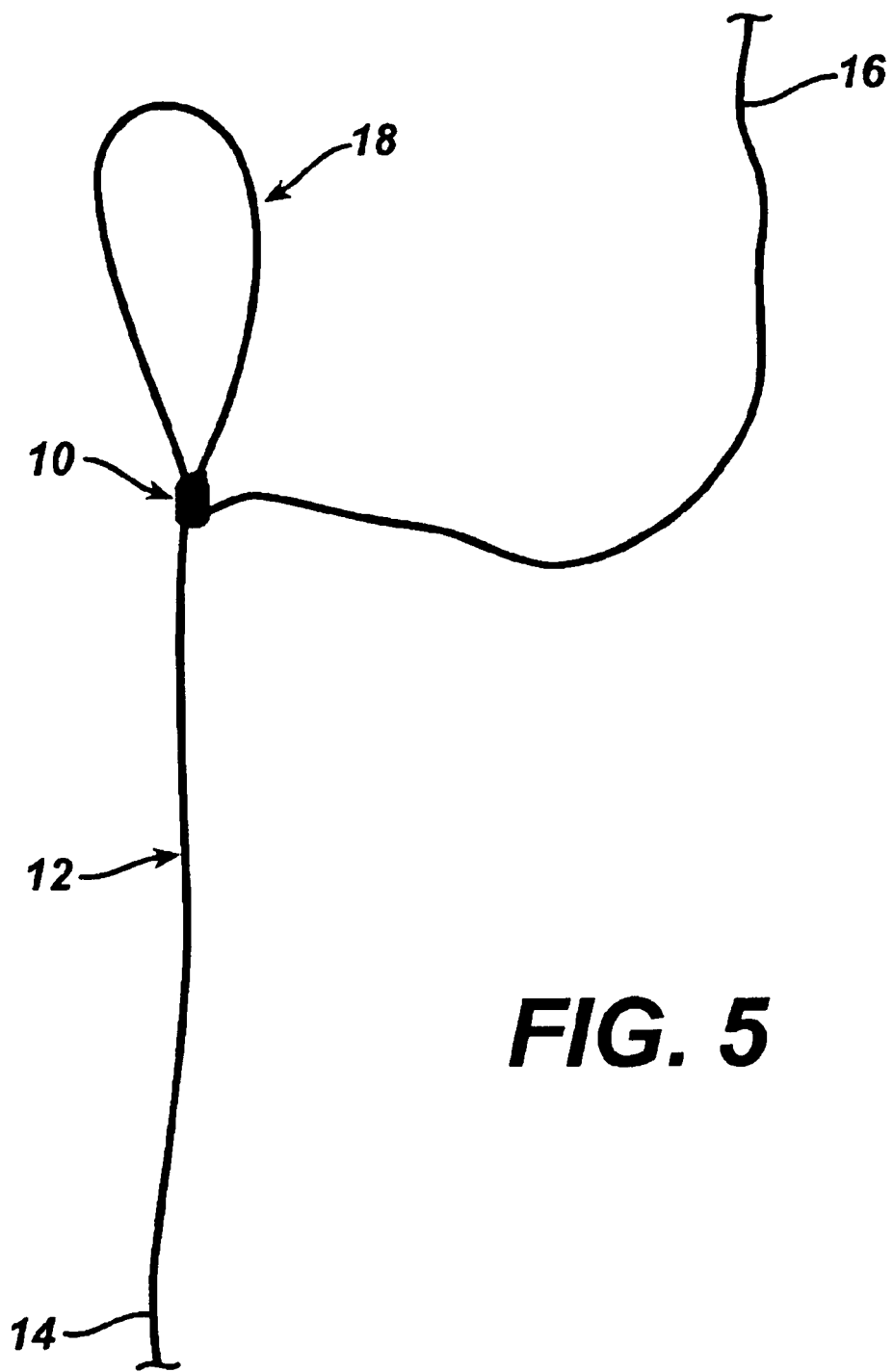
FIG. 5 shows a loosely formed sliding and locking knot of the present invention.
Figure 6:
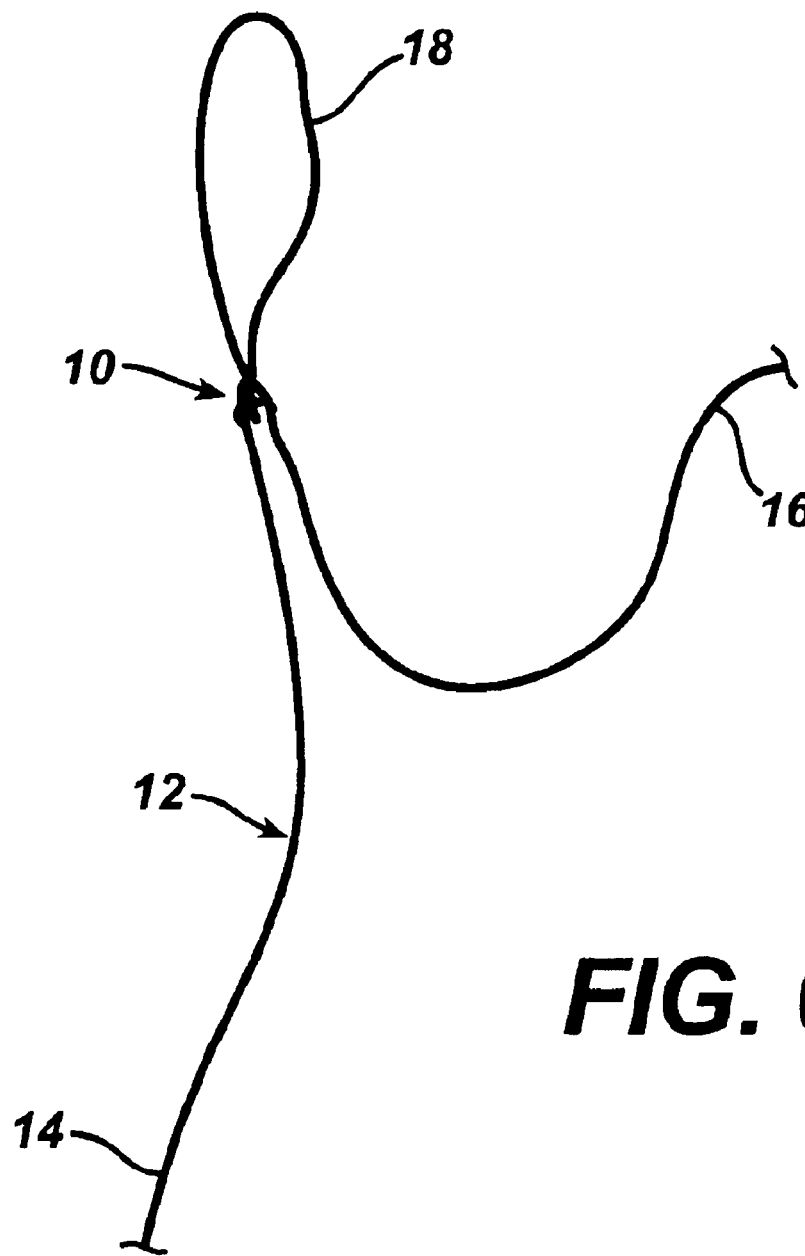
FIG. 6 shows the knot of FIG. 5 slid forward.
Figure 7:
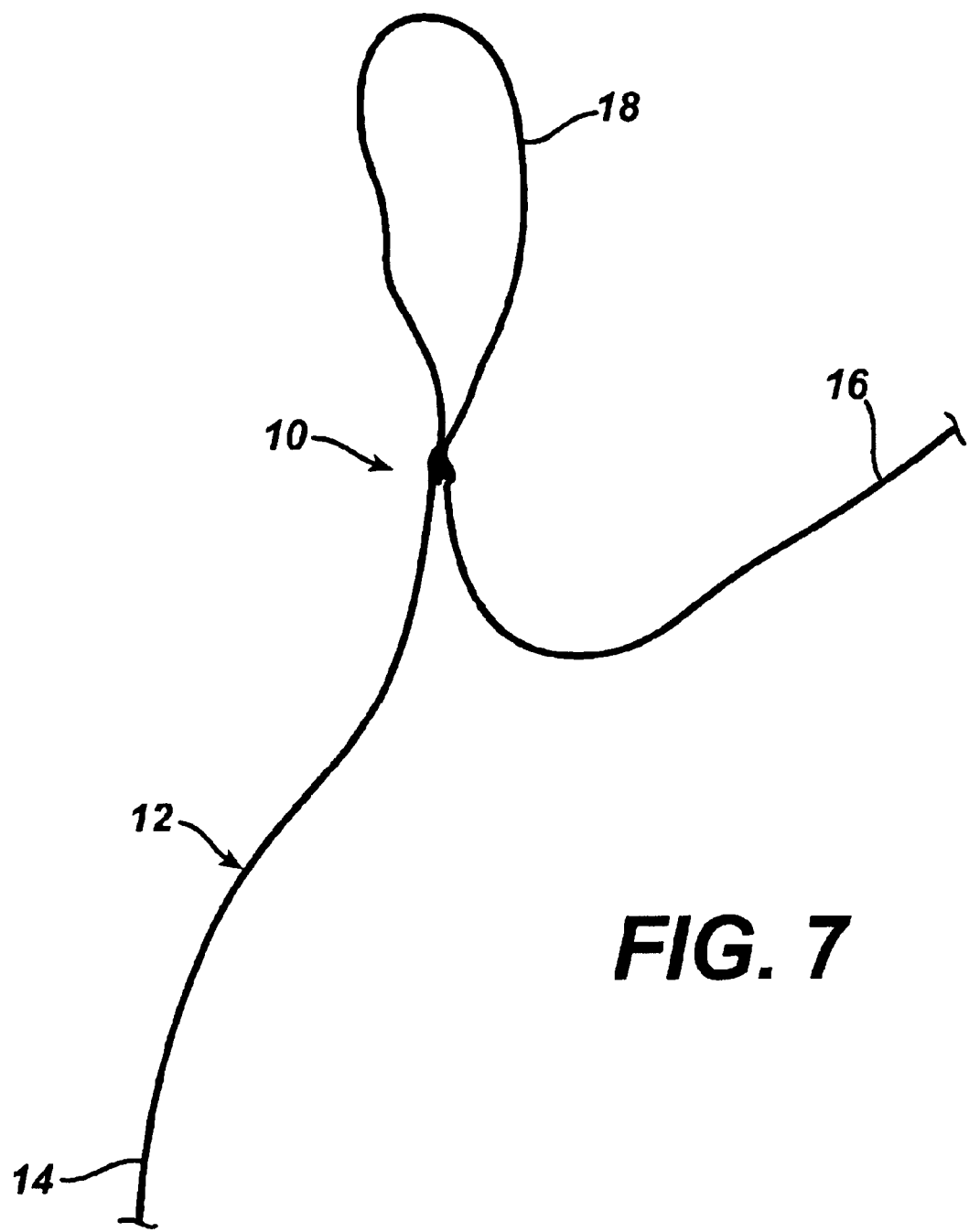
FIG. 7 shows the sliding and locking knot of FIG. 6 locked.

When the last coil 26 has been made, the terminal end 16 may next be threaded through second loop 20 as illustrated in FIG. 4. The terminal end 16 can then be pulled slightly to close the proximal loop 18*b* and move coils 22, 24, and 26 together, forming a loosened knot 10 as shown in FIG. 5. It is desirable not to over tighten the knot 10 at this stage, in order to avoid bunching of the filament 12. The looseness of the knot 10 facilitates its ability to slip down post 14. Referring to FIG. 6, the knot 10 is slid forward by pulling on the post 14 to enable knot 10 to glide down post 14. When the knot 10 is positioned at the desired location, it is possible to easily and quickly lock the knot 10 by pulling on the terminal end 16 of the filament 12, as shown in FIG. 7.

Figure 8:
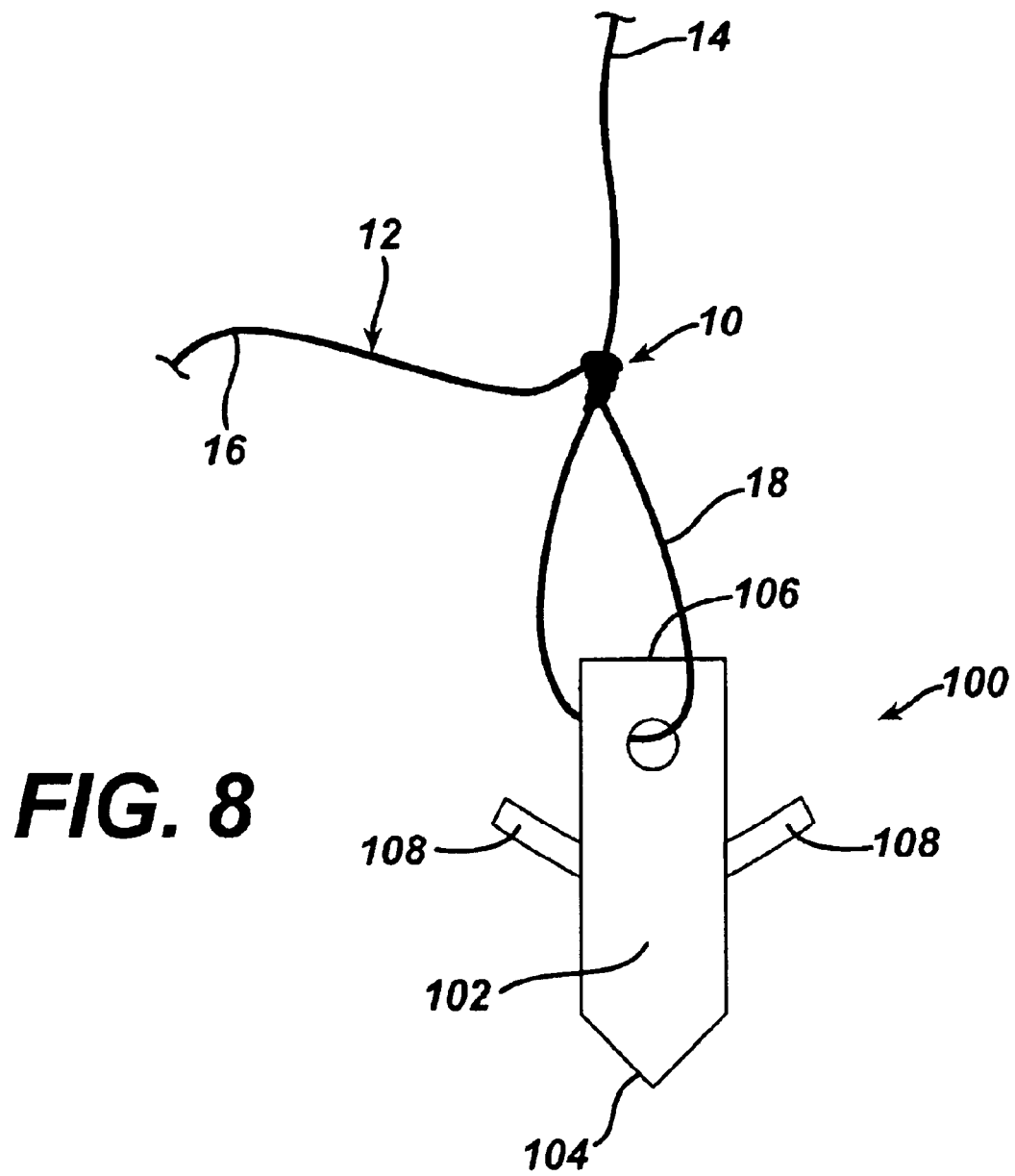
FIG. 8 shows an exemplary bone anchor with the sliding and locking knot of the present invention.

The sliding and locking knot 10 of the present invention can be used with surgical devices such as bone or tissue anchors and other suture retaining structures. For example, filament 12 may be threaded through a bone anchor 100 prior to forming first loop 18 so that the sliding and locking knot 10 is attached to the mechanical support, as shown in FIG. 8. Conventional bone anchors suitable for use with the sliding and locking knot include at least those described in U.S. Pat. Nos. 5,782,866 and 5,522,845 issued to Wenstrom, Jr. and U.S. Pat. No. 5,441,502 issued to Bartlett, and incorporated herein by reference. FIG. 8 illustrates a typical bone anchor having a tubular elongate body 102 extending between a first leading end 104 and a second trailing end 106. A pair of bone engaging members 108 extends from the tubular elongate body 102. A suture receiving aperture 110 within the elongate body 102 enables a strand or filament of suture 12 to be threaded therethrough. Once attached to the tubular elongate body 102, the suture may be pulled to manipulate the bone anchor after it is inserted into the bone cavity.

Figure 9A:
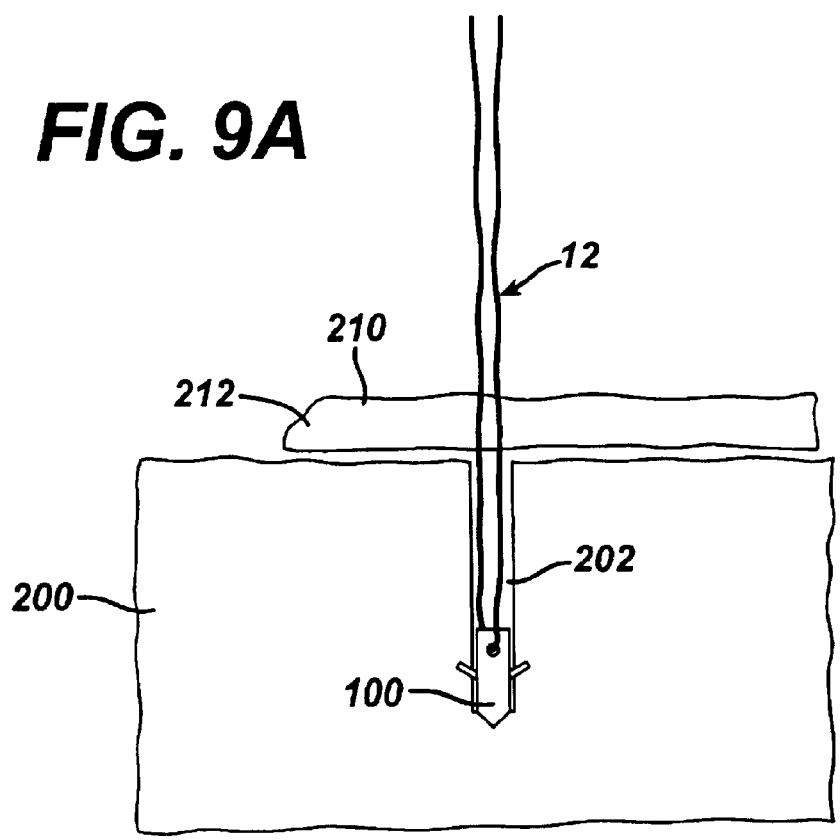
FIG. 9A depicts a method for attaching a soft tissue to bone.
Figure 9B:
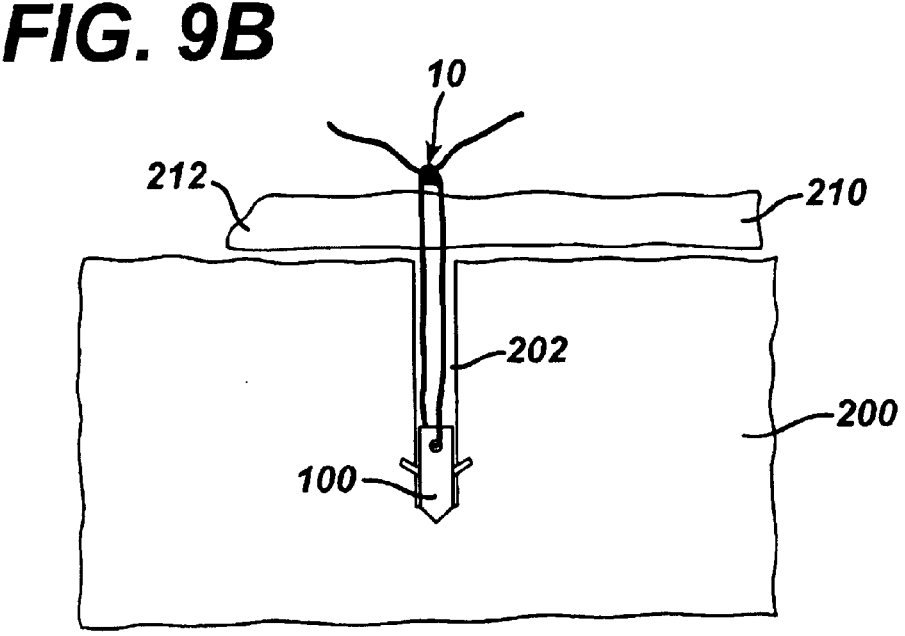
FIG. 9B depicts another method for attaching a soft tissue to bone.

FIGS. 9A and 9B illustrate two applications of the sliding and locking knot of the present invention with bone anchor 100 where a soft tissue such as a torn ligament 210 needs to be reattached to surrounding bone 200. In FIG. 9A, the bone anchor 100 is provided with filament 12 for reattaching the tissue 210 to the bony structure 200. Bone anchor 100 and filament 12 can be threaded through ligament 210 to hold the tissue 210 in place prior to tying the filament 12 into a knot 10. Alternatively, bone anchor 100 can be inserted and engaged within bone cavity 202, while proximal and distal ends 14, 16 of filament 12 are allowed to extend from the bone cavity 202 around soft tissue 210. The filament 12 can then be tied to form sliding and locking knot 10 of the present invention after the soft tissue 210 is in place. While the illustrated embodiment shows an anchor having two bone engaging members, a person of ordinary skill will recognize that a variety of known bone anchors may be used with the invention including those that engage a bone using expanding elements or by changing orientation within a bone tunnel below a layer of cortical bone.

Under certain circumstances, it is preferable to provide the bone anchor 100 with a preformed knot 10 on the filament 12. For instance, where the surgery has to be performed under severe time constraints, it may be more expedient to use a bone anchor 100 having a preformed knot 10. In such a situation, the free end 212 of the ligament 210 can be placed within the major loop 18 of the sliding and locking knot 10, as shown in FIG. 9B. The sliding and locking knot 10 may be attached to the bone anchor 100 so that when the anchor is inserted into a bone cavity 202 within the bony structure 200, the sliding and locking knot 10 can be slid down the post 14 to bring the torn ligament 210 proximate to the bony structure 200. Once the ligament 210 is properly positioned, the sliding and locking knot 10 can then be locked.

Sliding and locking knot 10 can also be formed alone to effect wound closure or to bring tissue together after filament 12 is threaded through the tissues using a conventional surgical needle so that loop 18 extends through the tissues to be brought together.

Strand or filament 12 used in the present invention may be constructed from thread suitable for use as a suture. A variety of surgical grade suture materials are well known to those of ordinary skill in the art. Exemplary materials include braided polyester and polydioxanone (PDS).

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. A method for forming a sliding and locking surgical knot, comprising:

forming a post at a proximal-most end of a filament and a major loop on the post;

threading a distal-most free end of the filament through the major loop to form a minor loop;

coiling the free end of the filament around the major loop after the minor loop has been formed to form at least one coil bisecting the major loop; and threading the free end of the filament through the minor loop.

2. The method of claim 1, wherein the step of coiling the free end of the filament is repeated to form a plurality of coils bisecting the major loop.

3. The method of claim 1, further comprising the step of pulling the post to slide the knot toward the free end.

4. The method of claim 1, further comprising the step of pulling the free end to lock the knot.

5. The method of claim 1, further comprising the step of threading the filament through a suture anchor device prior to forming the major loop.

6. The method of claim 1, further comprising the step of threading the filament through tissue prior to forming the major loop.

7. A sliding and locking surgical knot, comprising:

a filament having at a proximal-most end a post including thereon a major loop, minor loop, and at least one coil encircling and bisecting the major loop; and a distal-most free end of the filament extending from the minor loop;

wherein pulling the free end effects tightening of the at least one coil about the major loop, minor loop, and post to create a knot which can be locked without the necessity for a half hitch.

8. The sliding and locking surgical knot of claim 7, wherein there are a plurality of coils encircling the major loop.

9. The sliding and locking surgical knot of claim 7, further including a suture anchor device.

10. The sliding and locking surgical knot of claim 7, wherein the filament is a surgical grade suture material.

11. A suture retaining structure, comprising:
   a body extending between a first leading end and a second trailing end, the body having thereon at least one bone engaging element;
   a suture receiving aperture within the body; and
   a sliding and locking surgical knot extending from the suture receiving aperture, the sliding and locking knot comprising:
      a filament having at a proximal-most end a post including thereon a major loop, minor loop, and at least one coil encircling and bisecting the major loop; and
      a distal-most free end of the filament extending from the minor loop;
      wherein pulling the free end effects tightening of the at least one coil about the major loop, minor loop, and post to create a knot which can be locked without the necessity for a half hitch.

12. A method for anchoring tissue to a bony structure, comprising:
   providing a suture retaining structure, comprising a body extending between a first leading end and second trailing end, the body having thereon at least one bone engaging element, a suture receiving aperture within the elongate body, and a sliding and locking surgical knot extending from the suture receiving aperture, the sliding and locking knot comprising a filament having at a proximal-most end a post including thereon a major loop, minor loop, and at least one coil encircling and bisecting the major loop, and a distal-most free end of the filament extending from the minor loop, wherein pulling the free end effects tightening of the at least one coil about the major loop, minor loop, and post to create a knot which can be locked without the necessity for a half hitch;
   placing a free end of the tissue through the major loop of the sliding and locking knot;
   inserting the suture retaining structure into a bone cavity within the bony structure;
   sliding the knot down the post to bring the tissue proximate to the bony structure; and
   locking the knot in place.

13. The method of claim 12, wherein the step of sliding the knot comprises pulling on the post.

14. The method of claim 12, wherein the step of locking the knot comprises pulling the free end of the filament.

15. A method for anchoring tissue to a bony structure, comprising:
   providing a suture retaining structure, comprising a body extending between a first leading end and second trailing end, the body having thereon at least one bone engaging element, and a suture receiving aperture within the elongate body;
   threading a suture filament through the suture receiving aperture;
   Inserting the suture retaining structure into a bone cavity within the bony structure;
   creating a sliding and locking knot by forming a post at a proximal-most end of the filament and a major loop on the post, threading a distal-most free end of the filament through the major loop to form a minor loop, coiling the free end of the filament around the major loop after the minor loop has been formed to form at least one coil bisecting the major loop, and threading the free end of the filament through the minor loop;
   placing a free end of a soft tissue through the major loop of the sliding and locking knot;
   sliding the knot down the post to bring the tissue proximate to the bony structure; and
   locking the knot in place.

16. The method of claim 15, wherein the step of sliding the knot comprises pulling on the post.

17. The method of claim 15, wherein the step of locking the knot comprises pulling the free end of the filament.

* * * * *